(12) United States Patent
Hammond et al.

(10) Patent No.: US 7,044,980 B2
(45) Date of Patent: May 16, 2006

(54) FACILITATING DRAINAGE

(75) Inventors: Gaines W. Hammond, Spartanburg, SC (US); Barry N. Gellman, North Easton, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 8 days.

(21) Appl. No.: 09/733,752

(22) Filed: Dec. 8, 2000

(65) Prior Publication Data
US 2002/0072788 A1    Jun. 13, 2002

Related U.S. Application Data

(60) Provisional application No. 60/180,131, filed on Feb. 3, 2000, provisional application No. 60/188,002, filed on Mar. 9, 2000.

(51) Int. Cl.
*A61F 2/04* (2006.01)
(52) U.S. Cl. ............... 623/23.66; 623/23.64; 604/533
(58) Field of Classification Search ........... 604/15, 604/103, 523, 533, 8, 104, 517; 623/1.11, 623/23.64, 23.66, 23.7, 1.36; 606/108
See application file for complete search history.

(56) References Cited

U.S. PATENT DOCUMENTS

| | | | |
|---|---|---|---|
| 3,923,066 A | 12/1975 | Francisoud et al. | 128/348 |
| 4,222,384 A | 9/1980 | Birtwell | 128/349 |
| 4,307,723 A | 12/1981 | Finney | 128/349 |
| 4,350,161 A | 9/1982 | Davis, Jr. | 128/349 |
| 4,432,757 A | 2/1984 | Davis, Jr. | 604/99 |
| 4,501,580 A | 2/1985 | Glassman | 604/43 |
| 4,553,959 A | 11/1985 | Hickey et al. | 604/96 |
| 4,655,771 A | 4/1987 | Wallsten | 623/1 |
| 4,660,560 A | 4/1987 | Klein | 128/344 |
| 4,713,049 A | 12/1987 | Carter | 604/8 |
| 4,732,152 A | 3/1988 | Wallsten et al. | 128/343 |
| 4,813,429 A | 3/1989 | Eshel et al. | 128/736 |

(Continued)

FOREIGN PATENT DOCUMENTS

EP    0 935 977    8/1999    ............ 25/4

(Continued)

OTHER PUBLICATIONS

"An overview of superelastic stent design" T.W. Deurig et al.—Minimally Invasive Therapy & Allied Technologies—vol. 9, No. (3/4), Aug., 2000, ISSN 1364-5706—pp. 235-246.

*Primary Examiner*—Brian E Pellegrino
(74) *Attorney, Agent, or Firm*—Robert J. Tosti; Steven M. Jensen; Edwards Angell Palmer & Dodge, LLP

(57) ABSTRACT

A prostatic stent comprises a body member and a retaining member. The body member includes a distal terminating end, a proximal end portion, and a lumen extending within the body member to allow fluid drainage through the body member. The body member is sized for placement substantially within the prostatic section of the urethra, with the distal terminating end located proximal of an external sphincter to allow normal operation of the external sphincter. The retaining member extends from the proximal end portion of the body member. The retaining member is collapsible into a first state to allow passage of the prostatic stent into the urethra, and the retaining member is expandable into a second state when located in a bladder to hold the body member in place substantially within the prostatic section of the urethra.

12 Claims, 19 Drawing Sheets

U.S. PATENT DOCUMENTS

| | | | |
|---|---|---|---|
| 4,813,935 A | 3/1989 | Haber et al. | 604/99 |
| 4,861,337 A | 8/1989 | George | 604/96 |
| 4,931,037 A | 6/1990 | Wetterman | 604/8 |
| 4,954,126 A | 9/1990 | Wallsten | 600/36 |
| 4,955,859 A | 9/1990 | Zilber | 604/8 |
| 4,973,301 A | 11/1990 | Nissenkorn | 604/8 |
| 4,994,066 A | 2/1991 | Voss | 606/108 |
| 4,995,868 A | 2/1991 | Brazier | 604/105 |
| 5,002,558 A | 3/1991 | Klein et al. | 606/192 |
| 5,007,898 A | 4/1991 | Rosenbluth et al. | 604/54 |
| 5,026,377 A | 6/1991 | Burton et al. | 606/108 |
| 5,030,227 A | 7/1991 | Rosenbluth et al. | 606/192 |
| 5,041,092 A | 8/1991 | Barwick | 604/104 |
| 5,059,169 A | 10/1991 | Zilber | 604/8 |
| 5,061,275 A | 10/1991 | Wallsten et al. | 623/1 |
| 5,078,720 A | 1/1992 | Burton et al. | 606/108 |
| 5,116,309 A | 5/1992 | Coll | 604/8 |
| 5,147,370 A | 9/1992 | McNamara et al. | 606/108 |
| 5,167,614 A | 12/1992 | Tessmann et al. | 604/8 |
| 5,178,148 A | 1/1993 | Lacoste et al. | 128/660.03 |
| 5,220,927 A | 6/1993 | Astrahan et al. | 128/785 |
| 5,221,253 A | 6/1993 | Coll | 604/8 |
| 5,224,953 A | 7/1993 | Morgentaler | 606/192 |
| 5,246,445 A | 9/1993 | Yachia et al. | 606/108 |
| 5,269,802 A | 12/1993 | Garber | 606/191 |
| 5,300,022 A | 4/1994 | Klapper et al. | 604/35 |
| 5,306,241 A | 4/1994 | Samples | 604/54 |
| 5,312,430 A | 5/1994 | Rosenbluth et al. | 606/192 |
| 5,322,501 A | 6/1994 | Mahmud-Durrani | 604/8 |
| 5,346,467 A | 9/1994 | Coll | 604/8 |
| 5,352,198 A | 10/1994 | Goldenberg et al. | 604/95 |
| 5,354,263 A | 10/1994 | Coll | 604/8 |
| 5,354,309 A | 10/1994 | Schnepp-Pesch et al. | 606/198 |
| 5,356,423 A | 10/1994 | Tihon et al. | 606/194 |
| 5,364,340 A | 11/1994 | Coll | 604/8 |
| 5,372,600 A | 12/1994 | Beyar et al. | 606/108 |
| 5,380,270 A * | 1/1995 | Ahmadzadeh | 604/8 |
| 5,391,196 A | 2/1995 | Devonec | 607/96 |
| 5,514,176 A | 5/1996 | Bosley, Jr. | 623/1 |
| 5,514,178 A | 5/1996 | Torchio | 623/12 |
| 5,520,697 A | 5/1996 | Lindenberg et al. | 606/108 |
| 5,540,713 A | 7/1996 | Schnepp-Pesch et al. | 606/198 |
| 5,601,591 A | 2/1997 | Edwards et al. | 606/198 |
| 5,609,583 A | 3/1997 | Hakki et al. | 604/282 |
| 5,624,395 A | 4/1997 | Mikhail et al. | 604/93 |
| 5,667,486 A | 9/1997 | Mikulich et al. | 604/8 |
| 5,674,241 A | 10/1997 | Bley et al. | 606/198 |
| 5,707,386 A | 1/1998 | Schnepp-Pesch et al. | 606/194 |
| 5,718,686 A | 2/1998 | Davis | 604/101 |
| 5,752,971 A * | 5/1998 | Rosenbluth et al. | 606/192 |
| 5,766,209 A | 6/1998 | Devonec | 604/8 |
| 5,776,161 A | 7/1998 | Globerman | 606/194 |
| 5,785,641 A | 7/1998 | Davis | 600/30 |
| 5,792,400 A | 8/1998 | Talja et al. | 264/103 |
| 5,817,102 A | 10/1998 | Johnson et al. | 606/108 |
| 5,830,179 A | 11/1998 | Mikus et al. | 604/49 |
| 5,833,707 A | 11/1998 | McIntyre et al. | 606/198 |
| 5,860,999 A | 1/1999 | Schnepp-Pesch et al. | 606/194 |
| 5,865,815 A | 2/1999 | Tihon | 604/280 |
| 5,876,417 A | 3/1999 | Devonec et al. | 606/192 |
| 5,916,195 A | 6/1999 | Eshel et al. | 604/96 |
| 5,928,208 A | 7/1999 | Chu et al. | 604/280 |
| 5,928,217 A | 7/1999 | Mikus et al. | 604/530 |
| 5,964,732 A | 10/1999 | Willard | 604/117 |
| 5,964,771 A | 10/1999 | Beyar et al. | 606/108 |
| 6,004,290 A | 12/1999 | Davis | 604/96 |
| 6,022,312 A | 2/2000 | Chaussy et al. | 600/29 |
| 6,033,413 A | 3/2000 | Mikus et al. | 606/108 |
| 6,053,897 A | 4/2000 | Sachse | 604/264 |
| 6,139,536 A | 10/2000 | Mikus et al. | 604/500 |
| 6,238,430 B1 * | 5/2001 | Klumb et al. | 623/1.11 |
| 6,254,570 B1 | 7/2001 | Rutner et al. | 604/101.02 |
| 6,258,060 B1 | 7/2001 | Willard | 604/117 |
| 2002/0065476 A1 | 5/2002 | Whalen et al. | 600/587 |
| 2002/0107540 A1 | 8/2002 | Whalen et al. | 606/192 |

FOREIGN PATENT DOCUMENTS

| | | |
|---|---|---|
| GB | 2348138 A * | 9/2000 |
| WO | 99/23952 | 5/1999 |
| WO | WO 99/30635 | 6/1999 |
| WO | WO 02/058541 A2 | 8/2002 |

* cited by examiner

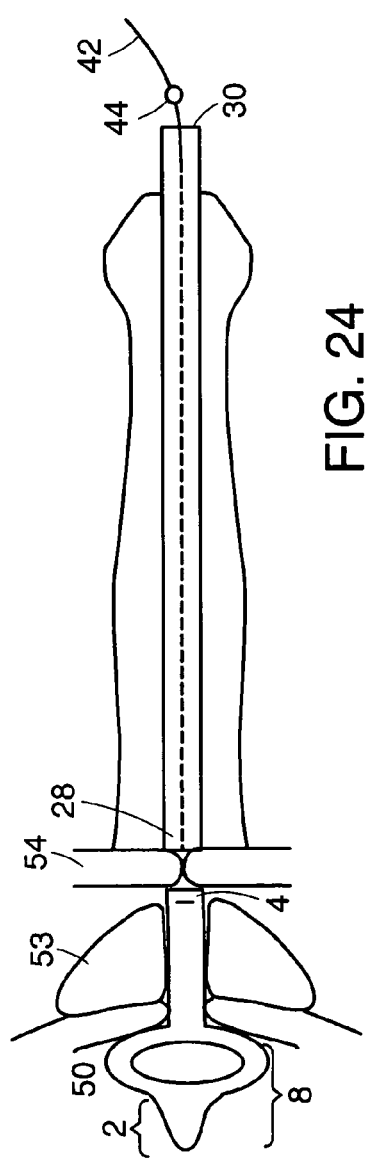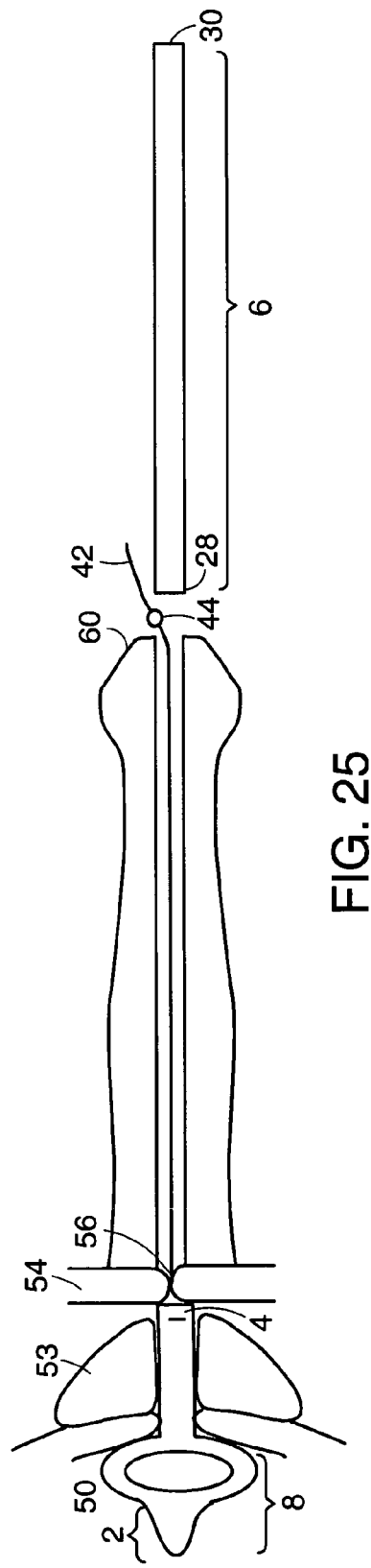
FIG. 24
FIG. 25

FACILITATING DRAINAGE

CROSS-REFERENCE TO RELATED APPLICATIONS

This claims priority to and the benefit of each of the following two provisional U.S. patent applications: Ser. No. 60/180,131 filed on Feb. 3, 2000, and Ser. No. 60/188,002 filed on Mar. 9, 2000.

TECHNICAL FIELD

This invention relates to facilitating drainage and, more particularly, to facilitating fluid drainage from the bladder and through the urethra of a patient.

BACKGROUND INFORMATION

The prostate is a gland in the male urinary system located directly below the bladder and around the urethra. In some men, especially men over fifty years of age, the prostate can become swollen or enlarged due to disease or infection. The enlarged prostate constricts the urethra causing discomfort and/or bladder outlet obstruction.

One of the known procedures for treating an enlarged prostate is thermal prostate therapy. During thermal prostate therapy, the prostate is heated above body temperature to remove the diseased tissue, whereby returning the prostate to normal size. Immediately after treatment, however, the prostate is still swollen or enlarged due to the therapeutic trauma induced by the procedure. It may take several weeks before the treated prostate recovers and no longer inhibits bladder drainage.

SUMMARY OF THE INVENTION

The invention involves providing drainage of fluid from the bladder of a patient. Systems and methods of the invention typically are used after the patient has undergone prostate treatment such as thermal therapy. Systems and methods according to the invention involve converting in situ a urinary drainage catheter into an indwelling device. The device maintains the prostatic section of the urethra open and able to pass fluid while also allowing normal operation of the patient's external sphincter such that the patient has full and normal control over the retention and discharge of urine from the bladder even with the device in place within the prostatic section of the urethra.

In general, in one aspect, the invention relates to a prostatic stent. The prostatic stent comprises a body member and a retaining member. The body member includes a distal terminating end, a proximal end portion, and a lumen extending within the body member to allow fluid to drain through the body member. The directional terms proximal and distal require a point of reference. In this application, the point of reference in determining direction is in the perspective of the patient. Therefore, the term proximal will always refer to a direction that points into the patient's body, whereas distal will always refer to a direction that points out of the patient's body. The body member is sized for placement substantially within the prostatic section of the urethra. The distal terminating end is positioned proximal of an external sphincter so as to allow normal operation of the external sphincter. The retaining member extends from the proximal end portion of the body member. The retaining member is collapsible into a first state to allow the passage of the prostatic stent into the urethra in the first instance. The retaining member also is expandable into a second state when located in the bladder to hold the body member in place substantially within the prostatic section of the urethra.

Embodiments of this aspect of the invention can include the following features. The retaining member of the prostatic stent can be tapered to provide comfort to the patient during insertion of the stent into the patient's urethra. The retaining member also can comprise two or more retaining arms, and the retaining arms can be biased in the second state. Prior to and during insertion of the prostatic stent into the patient's urethra, the retaining member is in the first state. The retaining member returns to substantially the second state once in the patient's bladder and thereby acts as an anchor to keep the body member of the prostatic stent substantially within the prostatic section of the urethra. The body member of the prostatic stent can include one or more side openings to allow fluid to drain from the prostatic section of the urethra into the lumen. To help prevent migration of the prostatic stent, the body member also can have one or more protrusions. The protrusions are designed to engage the wall of the prostatic urethra and thereby provide a source of friction that limits the motion of the prostatic stent within the urethra. The body member also can include a suture attached to the distal terminating end. The suture should be long enough to extend from the body member to the patient's meatus. The prostatic stent can be removed easily from the patient's body by pulling on the suture. The end of the suture can be connected to a ball, ring, coil, or other structure that either extends out of the body entirely or is located within the meatus. The point of the ball, ring, coil or other structure at the end of the suture is to facilitate location of the end of the suture and then removal of the stent by the patient himself or by a medical professional, simply by pulling on the located suture.

In another aspect, the invention relates to a prostatic stent-catheter system for draining fluid from the bladder, through the prostatic urethra, and out of the patient's body. The prostatic stent-catheter comprises a stent and a connecting segment. The stent includes a body member comprising a distal terminating end, a proximal end portion, and a lumen extending within the body member. The body member is sized for placement substantially within the prostatic section of the urethra with the distal terminating end located proximal of the external sphincter to allow normal operation of the external sphincter. The connecting segment comprises an elongated body member including a distal end, a proximal end, and a lumen. The proximal end of the connecting segment is releasably coupled to the distal terminating end of the stent. The prostatic stent-catheter system has at least two modes of operation after being inserted into the patient's urethra. In a first mode, the stent and connecting segment are coupled together, and drainage of fluid from the bladder occurs continuously. In a second mode, the connecting segment is decoupled from the stent in situ, and the connecting segment then is removed from the patient's urethra. After the connecting segment is removed from the patient's body, the patient's external sphincter contracts and is allowed to function normally to allow the patient have full control over voiding of urine.

Embodiments of this aspect of the invention can include the following features. The stent portion of the prostatic stent-catheter can further include a retaining member extending proximally away from the body member. When the stent-catheter system is properly positioned, the retaining member will be located in the patient's bladder. In one embodiment the retaining member comprises a proximal curved tip that acts as an anchor within the bladder opening to prevent the distal migration of the stent. In another embodiment, the retaining member includes at least two retaining arms biased in an expanded state. The retaining arms are collapsible and are collapsed prior and during the insertion of the prostatic stent-catheter into the patient's urethra. The retaining arms in the present embodiment return to the expanded state once located in the patient's bladder and thereby act as an anchor to prevent stent migration. The contraction and the expansion of the retaining arms can be controlled through a pushing device while the prostatic stent-catheter is within the patient's body. The stent portion of the prostatic stent-catheter system can further include a body member comprising of a large pore mesh. The large pore mesh can be fabricated from any biocompatible, self-expanding material such as a nickel-titanium based alloy. The body member including the large pore mesh frictionally engages the patient's prostate, whereby anchoring the stent to prevent migration.

In general, in still another aspect, the invention relates to a method of placing a prostatic stent-catheter system within the urethra. The prostatic stent-catheter system, which includes a stent and a connecting segment releasably coupled to one another, is inserted into the urethra of the patient. A medical professional such as a physician advances the prostatic stent-catheter system through the urethra until at least a portion of the stent is positioned substantially within the prostatic section of the urethra. When properly positioned, at least a portion of the stent will reside within the prostatic section of the urethra, while the connecting segment will extend through the external sphincter, through the rest of the urethra, and outside of the patient's body. The physician will know that the prostatic stent-catheter system is properly positioned when urine or other bodily fluid is observed draining through the distal end of the connecting segment. Bodily fluids such as urine and blood draining through the prostatic stent-catheter system are monitored. If the procedure is being done after treatment (e.g., surgery) on the prostate, the medical professional must determine when the patient's prostate has recovered or is recovering sufficiently from the treatment, and then the professional decouples the connecting segment from the stent and withdraws the connecting segment entirely from the patient's body. The stent thus remains within the prostatic section of the urethra to prevent bladder outlet obstruction and to keep the prostatic section of the urethra open and passing fluid(s) from the bladder while allowing normal operation of the patient's external sphincter. Once the prostate has fully recovered and poses no risk of obstructing fluid drainage, the stent can be removed. Removal of the indwelling stent can be accomplished by pulling on a suture attached to the stent. The suture typically is left extending from the urethra outside of the patient's body, or it can be left just within the meatus and therefore easily located by the patient himself or a medical professional such as a doctor or nurse.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 24 is a schematic view illustrating connecting segment decoupling from the prostatic stent-catheter system of FIG. 19.

FIG. 25 is a schematic view illustrating connecting segment removal from the male urinary system.

DESCRIPTION

The invention generally relates to relieving bladder outlet obstruction. After prostate treatment, a patient can experience urinary retention. The invention generally involves treating urinary retention, especially male urinary retention, while still allowing normal operation of the patient's external sphincter (and thus allowing normal voiding of the bladder) even with a stent located temporarily within the prostatic section of the patient's urethra.

After a medical procedure to treat an obstructed prostate, such as thermal prostate therapy, a patient may experience prostate bleeding while the recently-treated prostate recovers. Another consequence of such medical procedures is bladder outlet obstruction which results from the still-slightly enlarged and recovering prostate. After the procedure, the medical professional (e.g., a physician) that performed the procedure or some other medical professional will monitor the amount of urine and prostate bleeding, and attempt to provide the patient with an open urinary passageway. In order to monitor continuously the bodily fluids from the patient's bladder and prostate, the medical professional(s) attending to the patient need(s) to prevent the patient's external sphincter from closing to allow constant and uninterrupted drainage of those bodily fluids. In general, the attending professional(s) only need(s) to monitor the flow of blood and urine from the patient's urinary system for a few hours. It may, however, take several weeks for the patient's prostate to recover. One of the objects of the present invention is to provide devices, systems, and methods which will maintain an open passageway throughout the patient's entire urinary system such that constant drainage can be realized for some period of time just after treatment of the prostate, and which also can thereafter provide an open urinary passageway from the bladder through the prostatic section of the urethra while simultaneously allowing normal operation of the patient's external sphincter such that the patient has full and normal control over bladder voiding.

Figure 1:
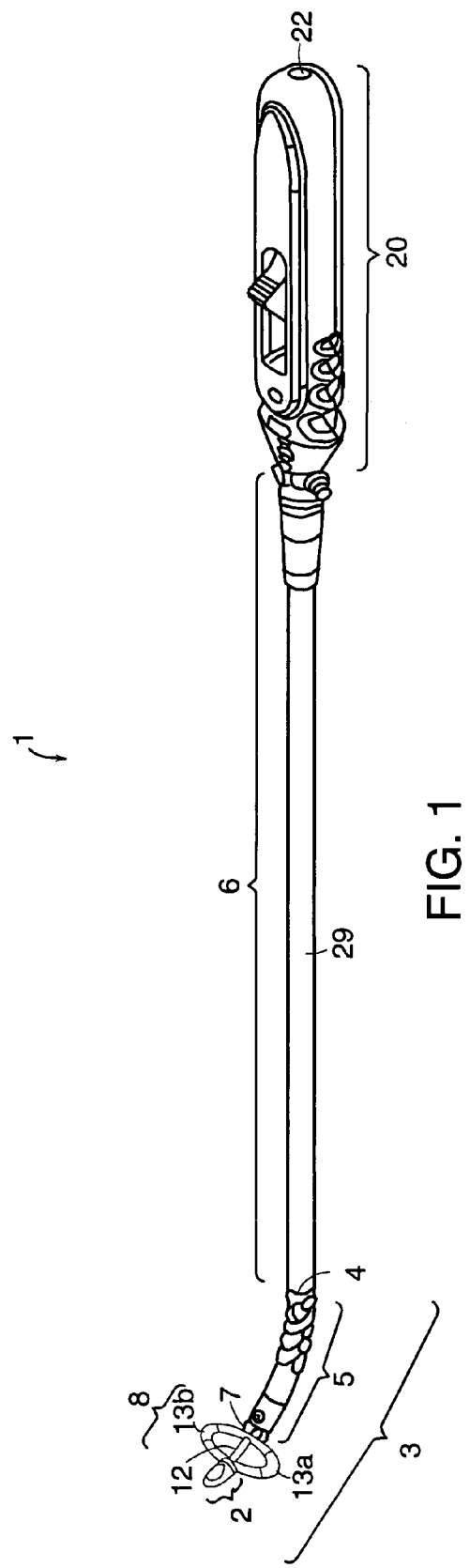
FIG. 1 is a schematic view of a prostatic stent-catheter system according to one embodiment of the present invention.
Figure 2:
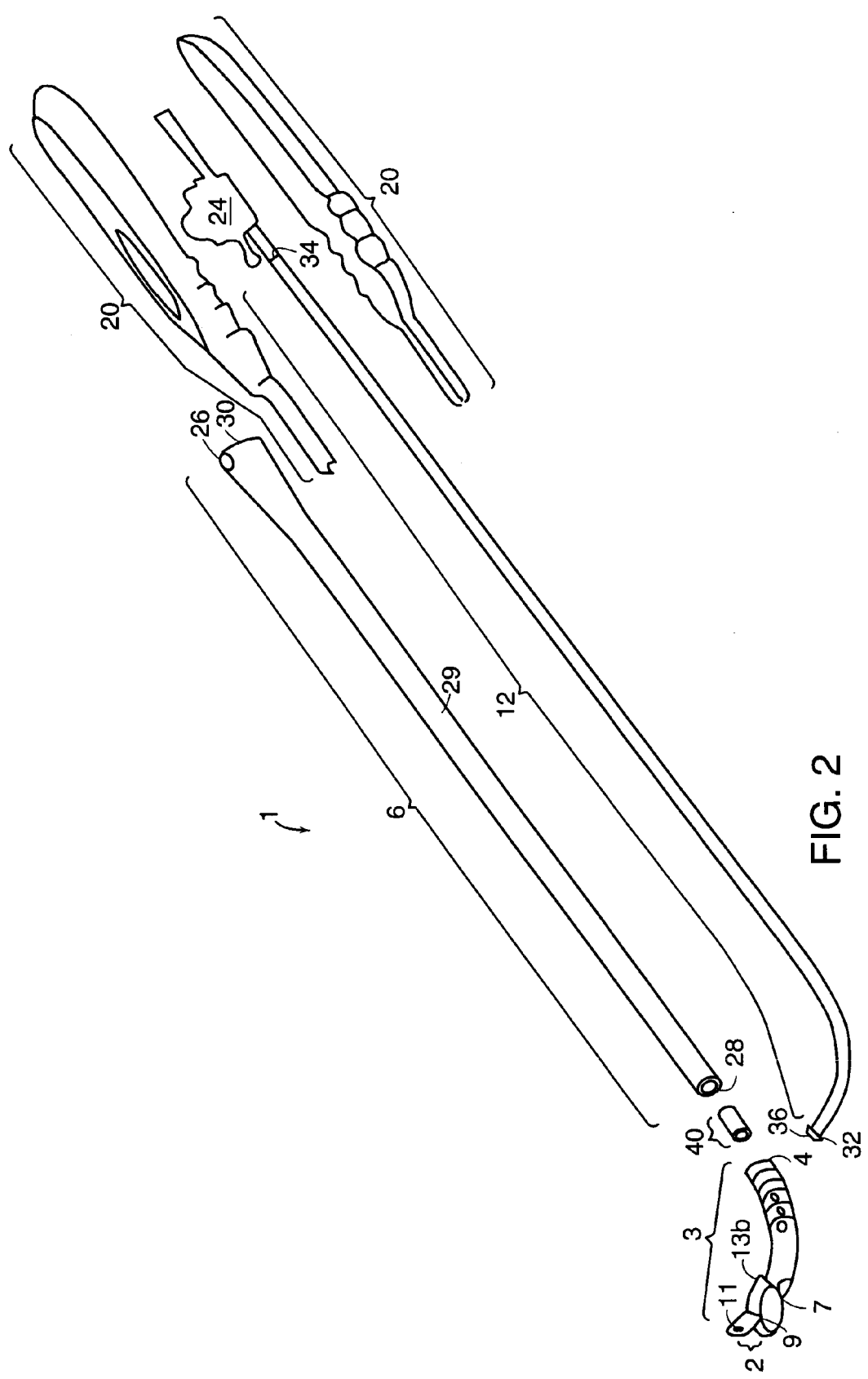
FIG. 2 is an exploded view of the prostatic stent-catheter system shown in FIG. 1.
Figure 3:
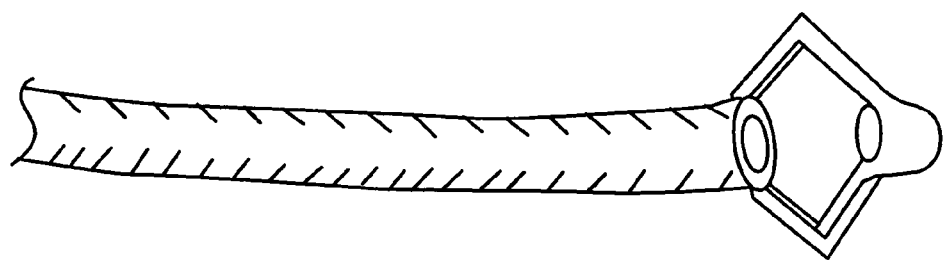
FIG. 3 is a schematic view of one embodiment of a prostatic stent.
Figure 4:
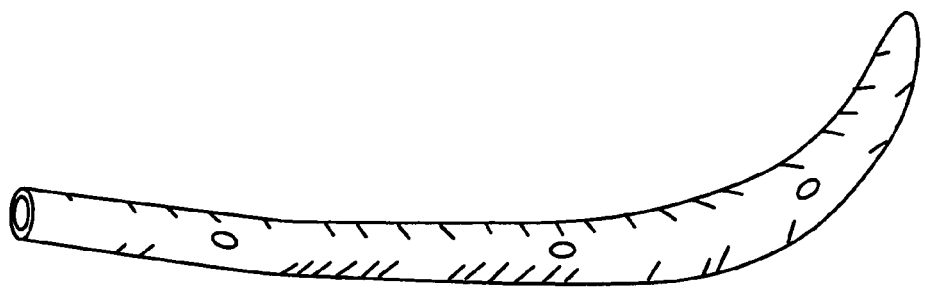
FIG. 4 is a schematic view of another embodiment of a prostatic stent.
Figure 5:
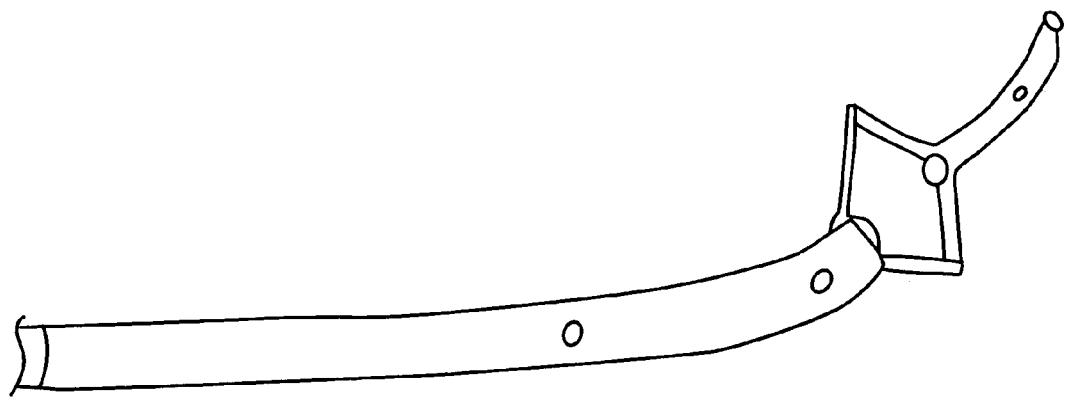
FIG. 5 is a schematic view of another embodiment of a prostatic stent.
Figure 6:
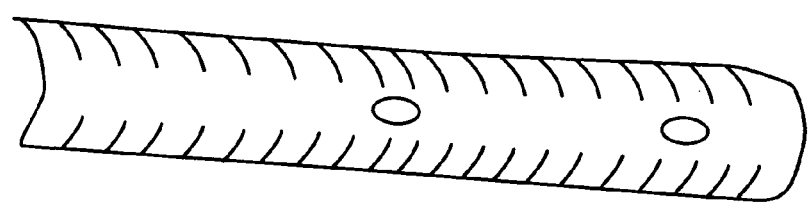
FIG. 6 is a schematic view of another embodiment of a prostatic stent.

Referring to FIGS. 1 and 2, a prostatic stent-catheter system 1 of the invention comprises a prostatic stent 3 and a connecting segment 6. The prostatic stent 3 includes a body member 5 made of one or more biocompatible materials such as silicone, nylon, polyglycolic acid, or stainless steel, and sized to fit substantially within the prostatic section of the urethra. The body member 5 has a proximal end 7, a distal terminating end 4, and a lumen extending from the proximal end 7 to the distal terminating end 4 to allow fluid drainage through the body member 5. As previously mentioned in this application, the term proximal refers to a direction that points into the patient's body and the term distal refers to a direction that points out of the patient's body. The body member 5 may be reinforced with a wire mesh to increase the tensile strength of the prostatic stent 3 whereby decreasing the possibility of the lumen collapsing. The prostatic stent 3 as illustrated in FIGS. 1 and 2 further comprises a retaining member 8. The retaining member 8 is also made from one or more biocompatible materials. In the disclosed embodiment, the retaining member 8 has at least two retaining arms 13a and 13b. Other retaining member 8 embodiments are possible, so long as these embodiments anchor the body member 5 within the prostatic section of the urethra, and do not inhibit fluid drainage from the bladder. Examples of some other retaining members are given in FIGS. 3–6. Other further possible embodiments of retaining member shapes include umbrella shaped prongs and a pigtail curl. All retaining member embodiments must be either collapsible or able to be straighten for insertion ease. Similarly, a retaining member is not required if a prostatic stent includes another means to prevent migration of the prostatic stent from the prostatic section of the urethra (for example, a body member that frictionally engages the patient's prostate). The retaining member 8, as shown as in the embodiment of the device in FIGS. 1–2, also includes a proximal tip 2. Within the proximal tip 2, there is a lumen extending from a base proximal tip opening 9 to a proximal tip opening 11. The retaining member 8 is collapsible and has at least two distinct states. In a first state, the retaining member 8 is collapsed to allow for insertion ease. In a second state, the retaining member 8 is expanded to secure the prostatic stent 3 from significant migration after the prostatic stent 3 has been properly positioned. The prostatic stent 3 is properly positioned within a male patient's urinary system, when the retaining member 8 is located within the patient's bladder and the body member 5 is located substantially within the prostatic section of the urethra with the distal terminating end 4 being located proximal to the patient's external sphincter. The connecting segment 6 of the prostatic stent-catheter system 1 comprises an elongated body member 29 having a proximal end 28 and a distal end 30. A lumen extends from the proximal end 28 to the distal end 30 for fluid drainage. At the distal end 30 of the connecting segment 6 there is at least one side opening 26 for fluid drainage.

During insertion of the prostatic stent-catheter system 1, the proximal end 28 of the connecting segment 6 is releasably coupled to the distal terminating end 4 of the prostatic stent 3. The coupling of the prostatic stent 3 with the connecting segment 6 creates a single lumen extending from the proximal end 7 of the body member 5 to the distal end 30 of the connecting segment 6. To couple the prostatic stent 3 to the connecting segment 6 a guide 40 is used. The guide 40 is an open ended tubular body member having a slightly smaller diameter than both the connecting segment 6 and the body member 5. The guide 40 is fastened to the proximal end 28 of the connecting segment 6 such that a portion of the guide 40 is within the lumen of the connecting segment 6 and the remaining portion extends out from the proximal end 28 of the connecting segment 6. The remaining portion of the guide 40 is then inserted into the lumen of the body member 5 creating a slip-fit seal between the prostatic stent 3 and the connecting segment 6. Various other couplings are possible, so long as the distal terminating end 4 of the body member 5 and the proximal end 28 of the connecting segment 6 are releasably joined together. For example, in other embodiments, the guide 40 is releasably coupled to the prostatic stent 3 with sutures that can be removed in situ after the prostatic stent 3 is properly positioned.

After a prostatic procedure to treat an obstructed prostate, such as thermal therapy, the patient's prostate typically will still be slightly enlarged and it may bleed. To prevent bladder obstruction and to monitor the amount of urine production and prostate bleeding, a physician can insert the prostatic stent-catheter 1 into a patient's urethra until the proximal tip 2 is located within the bladder and the connecting segment 6 extends through the external sphincter as to allow constant drainage of fluids from the patient's bladder and through the patient's prostate. Once the physician has decided that the patient's bodily fluids no longer need to be monitored, constant fluid drainage from the patient's bladder is no longer necessary. To avoid the potential risk of bladder retention due to the slightly enlarged and recently treated prostate, however, the physician may wish to maintain the prostatic stent 3 within the prostatic section of the urethra until the prostate is completely resolved. The physician, realizing that patient's prostate could take several weeks to resolve and not wishing to inconvenience the patient, can remove the connecting segment 6 from the prostatic stent-catheter system 1 while leaving the prostatic stent 3 in place by simply pulling on the connecting segment 6.

Figure 7:
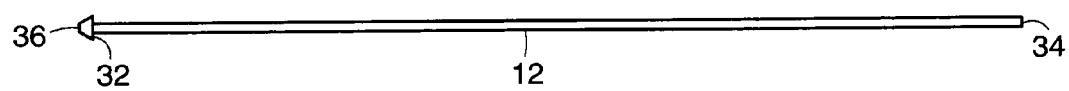
FIG. 7 is a schematic view of one embodiment of a pushing device of a prostatic stent-catheter system according to the invention.
Figure 8:
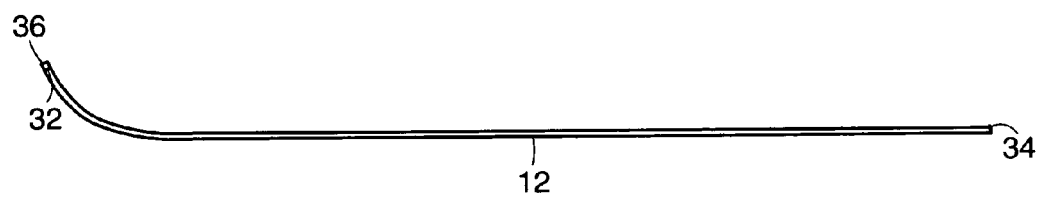
FIG. 8 is a schematic view of another embodiment of a pushing device.
Figure 9:
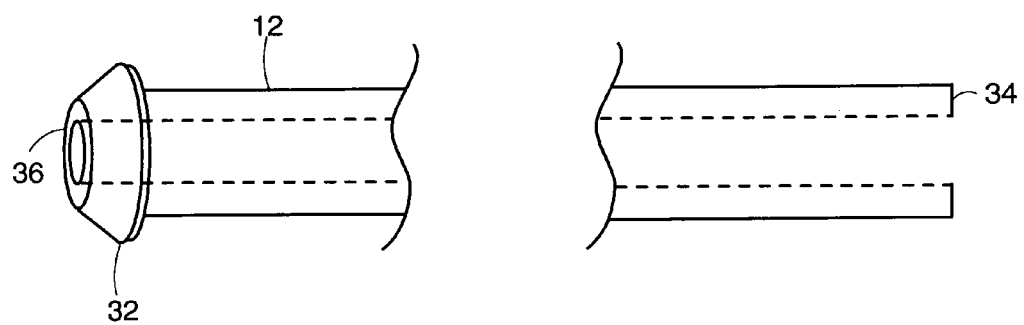
FIG. 9 is an enlarged view of the proximal end of one embodiment of a pushing device.

The embodiment of the prostatic stent-catheter system 1 of FIGS. 1 and 2 further comprises a pushing device 12 and a handle 20. The pushing device 12 has a proximal end 36 and a distal end 34. The width of the pushing device 12 is sized to fit within the lumens of the prostatic stent 3 and the connecting segment 6; while the length of the pushing device 12 is sized so that the proximal end 36 can contact the proximal tip 2 of the prostatic stent 3 while the distal end 34 extends beyond the distal end 30 of the releasably connected connecting segment 6. Therefore, the physician performing the procedure can use the pushing device 12 to contact the proximal tip 2 of the prostatic stent 3 once the prostatic stent-catheter system 1 is already inserted into the patient's body. The pushing device 12 can be made from any material that is flexible enough to conform to the patient's anatomy, but also rigid enough to extend the proximal tip 2 away from the body member 5. Materials such as stainless steel or polycarbonate meet these criteria. The pushing device 12 can be either straight as shown in FIG. 7 or curved as shown in FIG. 8, to aid in the insertion and placement of the prostatic stent 3 within the pro static section of the urethra. Extending through the entire pushing device 12 is a lumen capable of receiving a guide wire. At the proximal end 36 of the pushing device 12 is a flange 32 used to connect the proximal tip 2 to the pushing device 12. The flange 32 also prevents premature separation of the pushing device 12 from the proximal tip 2. The flange 32 is best illustrated in FIG. 9. The other end of the pushing device 12, the distal end 34, is attached to a mechanism 24 located within the handle 20. The mechanism 24 is slidably movable in the proximal and distal directions. Because the mechanism 24 is attached to the pushing device 12, the position of the mechanism 24 determines the position of the pushing device 12 within the pro static stent-catheter system 1. The handle 20 is attached to the distal end 30 of the connecting segment 6 and remains outside of the patient's body. Therefore, a physician has access to the position of the pushing device 12 at all times during a procedure. Besides the mechanism 24, the handle 20 also includes at least one opening 22 for drainage of fluids from the prostatic stent-catheter system 1.

Figure 10:
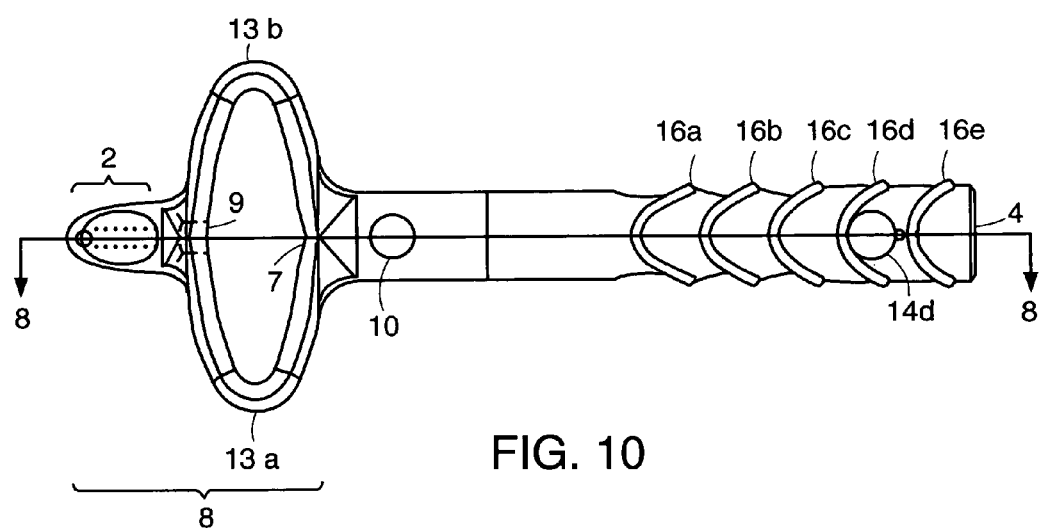
FIG. 10 is an enlarged plan view of a prostatic stent.
Figure 11:
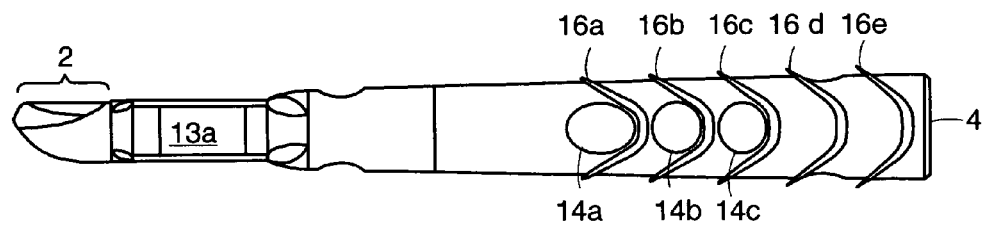
FIG. 11 is a side view of the prostatic stent shown in FIG. 10.
Figure 12:
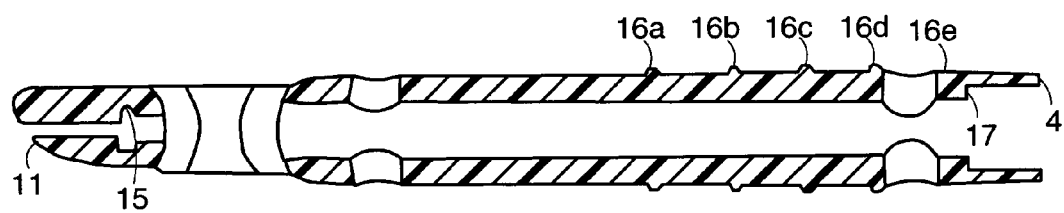
FIG. 12 is a cross-sectional view of the prostatic stent taken along the lines 8—8 in FIG. 10.

The embodiment of the prostatic stent 3 of FIGS. 1 and 2 includes a series of openings 10, 14a–14d in communication with the lumen of the body member 5, and a series of protuberances 16a–16e. These features are most clearly illustrated in FIGS. 10–12. The series of openings 10, 14a–14d and/or the series of protuberances 16a–16e on the body member 5 decrease the likelihood of migration of the prostatic stent 3. The protuberances may be parallel to each other or may be progressively angled to further decrease migration. In the disclosed embodiment, the series of protuberances 16a–16e have a serpentine pattern, however other possible patterns such as circular or spiral are possible. When the prostatic stent 3 is properly positioned, the series of protuberances 16a–16e are in contact with the patient's prostate. Consequently, the series of protuberances 16a–16e create a source of friction between the prostatic stent 3 and the prostate which decreases movement of the prostatic stent 3. The series of openings 10, 14a–14d in the body member 5 also create friction between the patient's prostate and the prostatic stent 3. The series of openings 10, 14a–14d further allow bodily fluids such as urine or blood to enter into the body member 5 of the prostatic stent 3 while permitting prostate tissue to extend into the prostatic stent 3 to aid in securing the prostatic stent 3 from migrating. To further prevent migration, the distal terminating end 4 may be belled outward to a diameter larger than the body member 5 but essentially equal to the connecting segment 6. FIG. 12 is a cross sectional view of the prostatic stent 3. In this drawing a proximal ledge 15 and a distal ledge 17 are noticeable in the internal prostatic stent 3 profile. The proximal ledge 15 is designed to receive the flange 32 of the pushing device 12 (shown in FIG. 9). The proximal ledge 15 provides a contact surface for the flange 32 to push against when the pushing device 12 is proximally extended. The distal ledge 17 is designed to receive the guide 40 (shown in FIG. 2). The distal ledge 17 provides a contact surface for the guide 40 to rest against while the prostatic stent 3 and the connecting segment 6 are coupled together.

Figure 13:
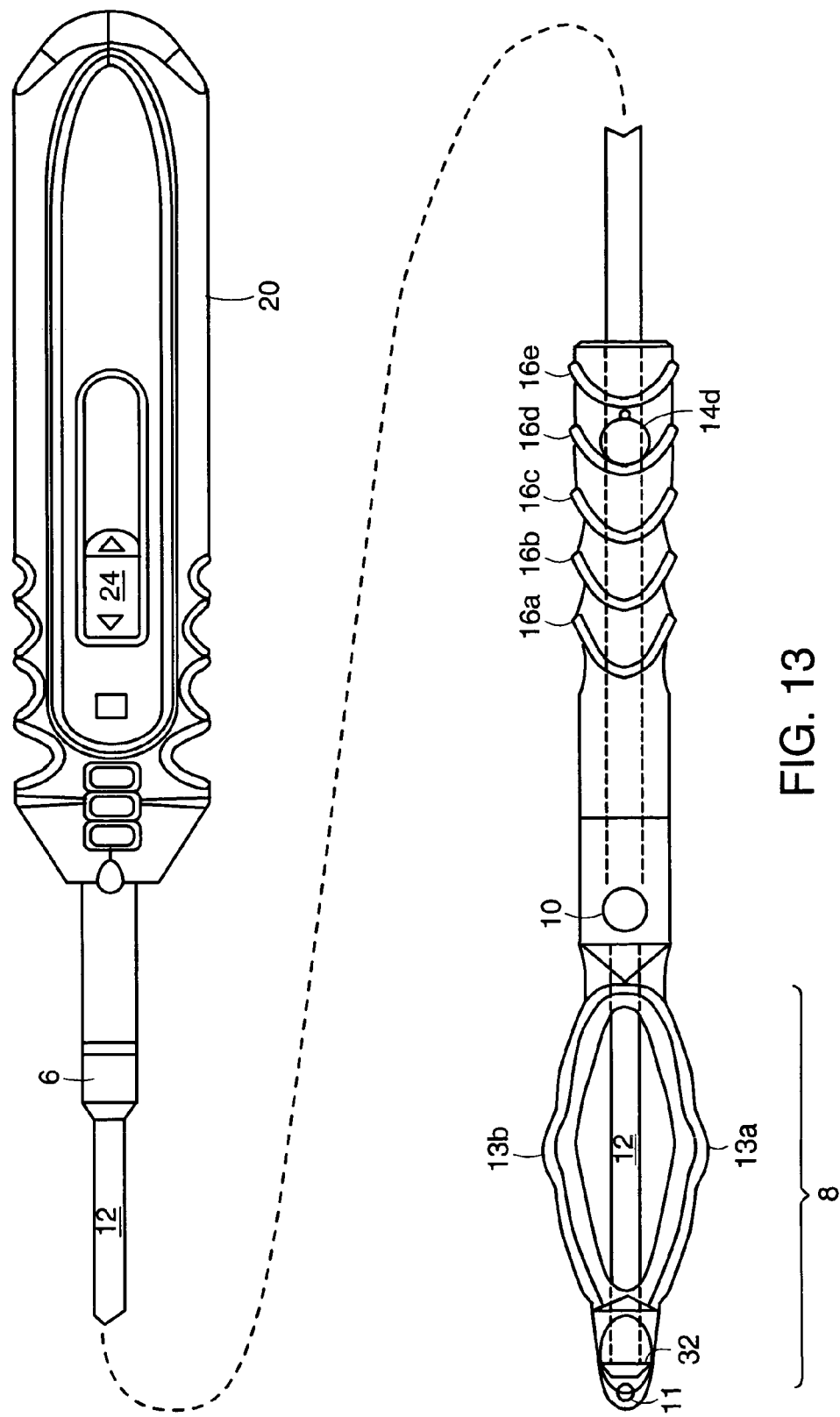
FIG. 13 is a schematic view of both a handle mechanism in a first position and a corresponding collapsed prostatic stent configuration with an engaged pushing device.
Figure 14:
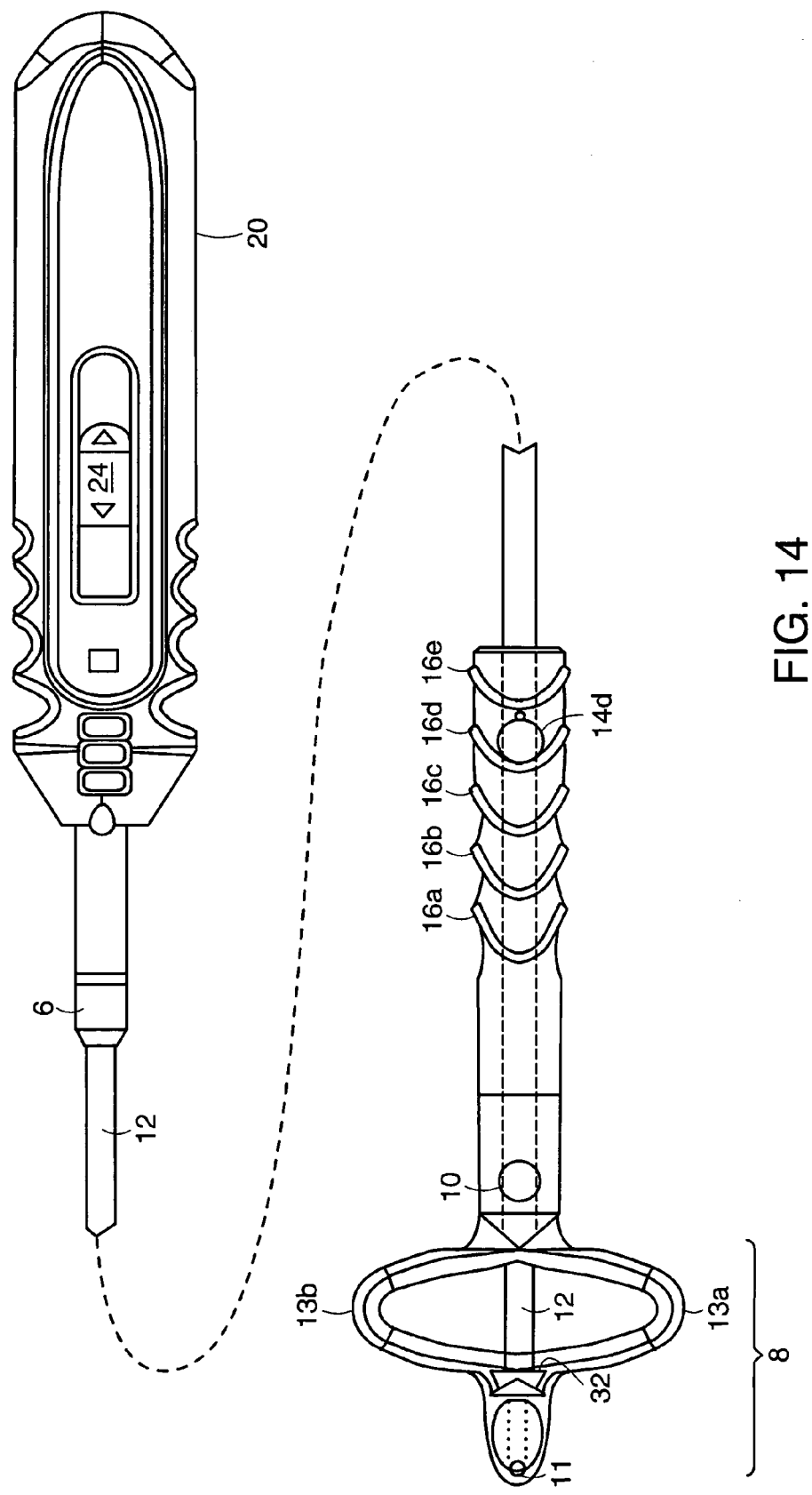
FIG. 14 is a schematic view of both a handle mechanism in a second position and a corresponding expanded prostatic stent configuration with an engaged pushing device.
Figure 15:
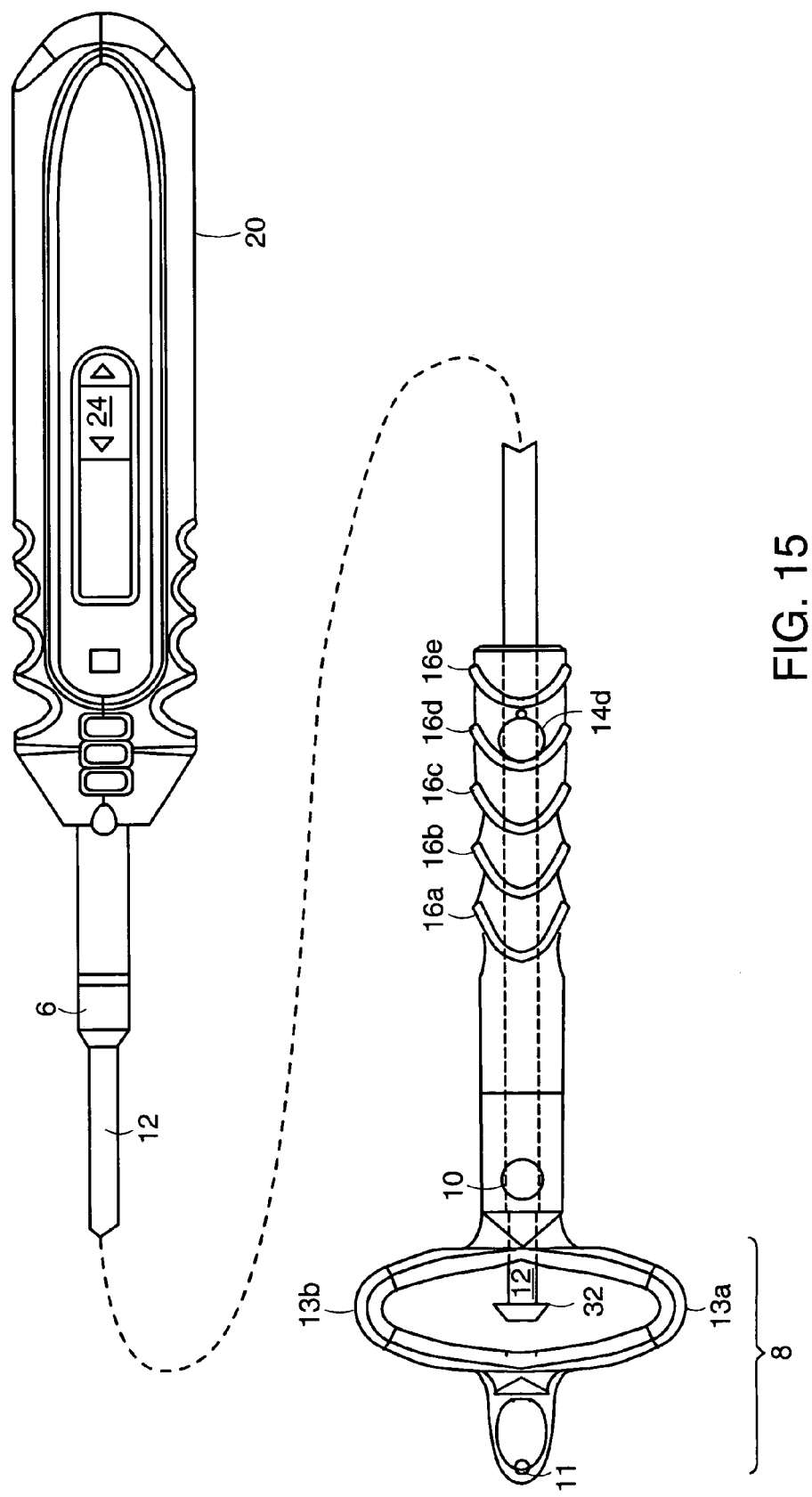
FIG. 15 is a schematic view of both a handle mechanism in a third position and a corresponding expanded prostatic stent configuration with a disengaged pushing device.

As previously discussed, the prostatic stent 3 as illustrated in FIGS. 1 and 2 includes a retaining member 8 with at least two distinct states. The retaining member 8 is biased in the second state. The physician can change the retaining member's 8 configuration to the collapsed or first state by either applying pressure with his or her fingers to the retaining arms 13a–13b to extend the proximal tip 2 in the proximal direction and thus collapse the retaining member 8 or by proximally extending the pushing device 12 within the lumen of the prostatic stent-catheter system 1 to extend the proximal tip 2 and thereby collapse the retaining member 8. In the latter case, the physician can control the process from outside of a patient's body by placing the mechanism 24 into a first position causing the extension of the pushing device 12. This process is schematically illustrated in FIG. 13. Similarly, the retaining member 8 can be returned to the second state by either removing the pressure on the retaining member 8 or retracting the pushing device 12 within the prostatic stent-catheter system 1. FIG. 14 shows the expansion of the retaining member 8 as a result of placing the mechanism 24 in a second position. To detach the pushing device 12 from the prostatic stent 3, the mechanism 24 is placed into a third position, shown in FIG. 15.

Figure 16:
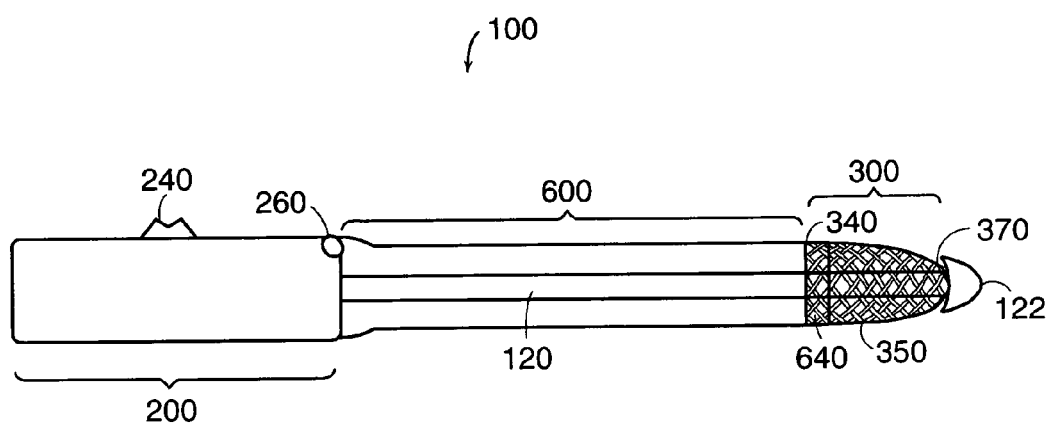
FIG. 16 is a plan view of another embodiment of a prostatic stent-catheter system, in an insertion configuration.
Figure 17:
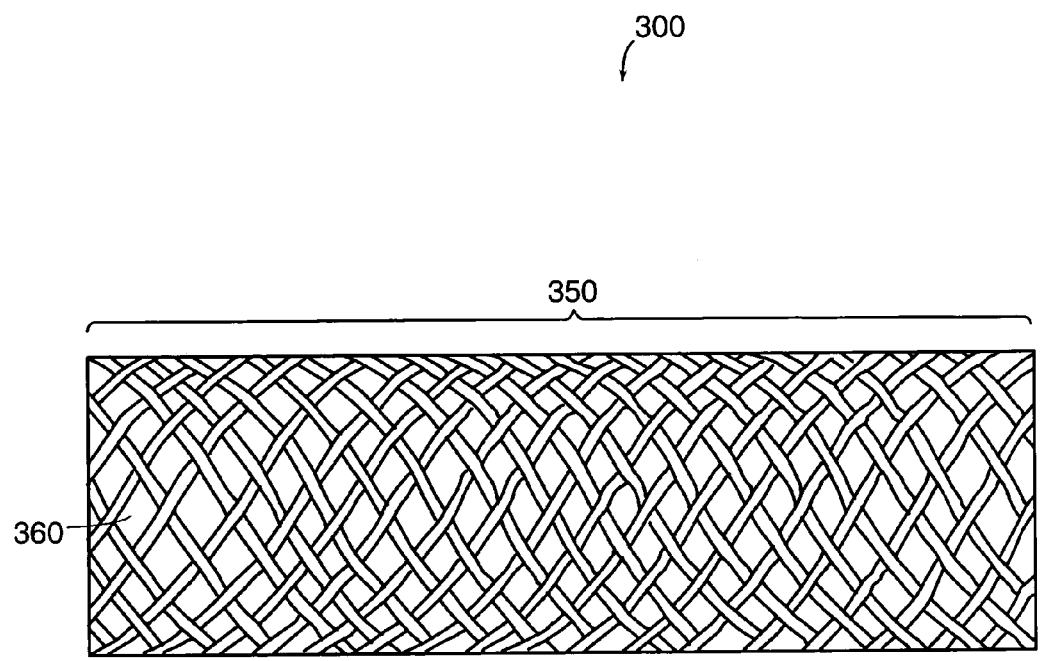
FIG. 17 is an enlarged plan view of the prostatic stent shown in FIG. 16.

Another embodiment of a prostatic stent-catheter system 100 is illustrated in FIG. 16. The prostatic stent-catheter system 100 comprises a prostatic stent 300 and a connecting segment 600. The prostatic stent 300 includes a large pore mesh design 350, a proximal end 370, a distal end 340, and a lumen extending between the proximal end 370 and the distal end 340. An enlarged view of the large pore mesh design 350 is illustrated in FIG. 17. The large pore mesh 350 is fabricated from any self-expanding, biocompatible material such as nylon, polyglycolic acid, stainless steel or nickel-titanium based alloys. The large pore mesh 350 is produced by weaving, braiding, or heat bonding strands of the selected self-expanding, biocompatible materials together or by slotting or pattern cutting by laser and/or conventional machining a hollow tube of the selected material. The large pore mesh 350 may be coated with a thin polymeric layer to prevent trauma to the patient's urethra during insertion. Each pore 360 in the large pore mesh is an opening for fluids to drain into the lumen of the prostatic stent 300. Because the prostatic stent 300 includes many pores, the possibility of all of the pores 360 becoming blocked by blood clots so as to inhibit drainage is small. The prostatic stent 300 is sized to fit within the prostatic section of the urethra. When properly positioned the proximal end 370 is located distal to the bladder while the distal end 340 terminates proximal to the external sphincter. In the disclosed embodiment, the prostatic stent 300 has a circular cross section. The shape of the cross section need not be circular. In other embodiments, a prostatic stent including a large pore mesh can have other cross sectional shapes such as a triangle or oval. In still yet other embodiments, the shape of a prostatic stent could differ from the disclosed embodiment by having a non-constant cross sectional shape such as hourglass or funnel shapes.

Figure 18:
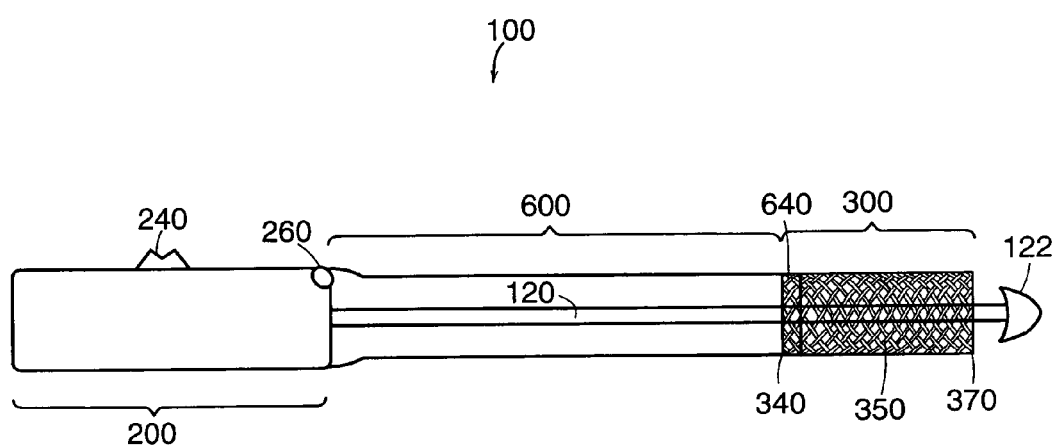
FIG. 18 is the prostatic stent-catheter system of FIG. 16 in a release configuration.

The prostatic stent-catheter system 100 of the embodiment illustrated in FIG. 16 further includes a guide 640 for coupling the prostatic stent 300 to the connecting segment 600, a handle 200 including an activation mechanism 240 and openings for fluid drainage 260, and a pushing device 120. The pushing device has a bullet-shaped proximal end 122. The bullet-shaped proximal end 122 is capable of capturing and collapsing the proximal end 370 of the prostatic stent 300. The opposite end of the pushing device is attached to the activation mechanism 240 in the handle 200. FIG. 18 illustrates the prostatic stent-catheter system 100 in a release configuration. The physician performing the procedure can achieve the release configuration by extending the pushing device 120 so that the bullet-shaped proximal end 122 releases the proximal end 370 of the prostatic stent 300. The physician can then remove the connecting segment 600 from the prostatic stent-catheter system 100 by decoupling the connecting segment 600 from the prostatic stent 300, and removing the connecting segment 600, the handle 200, and pushing device 120 from the patient's urethra.

The prostatic stent-catheter system 100 illustrated in FIG. 16 is placed into the patient's body, used in the patient's body, and removed from the patient's body in the same way that the other embodiments of prostatic stent-catheter systems described herein are placed, used, and removed.

Figure 19:
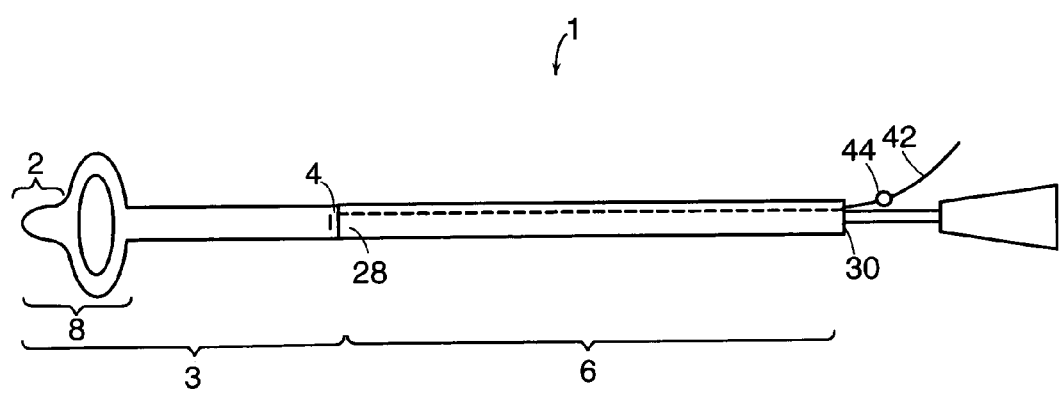
FIG. 19 is a schematic view of the prostatic stent-catheter system of FIG. 1, showing the prostatic stent-catheter system in an expanded configuration.
Figure 26:
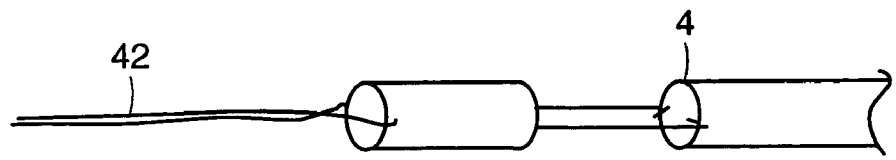
FIG. 26 is an enlarged schematic view of one embodiment of a retaining device.
Figure 27:
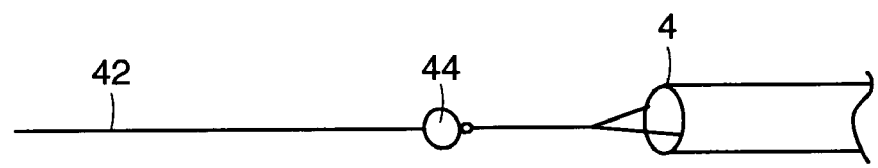
FIG. 27 is an enlarged schematic view of another embodiment of a retaining device.
Figure 28:
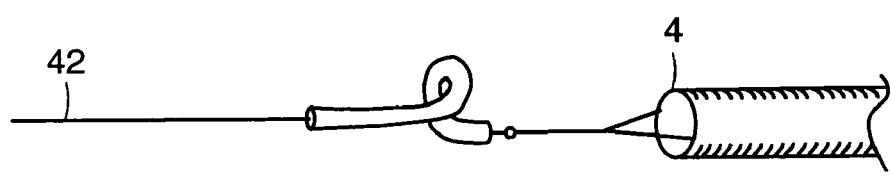
FIG. 28 is an enlarged schematic view of another embodiment of a retaining device.

The prostatic stent-catheter system 1 in FIGS. 19–25 is of the embodiment illustrated in FIGS. 1 and 2. In this embodiment, the prostatic stent 3 further comprises a retaining member 8 as previously described. In FIG. 19, the prostatic stent 3 in this invention is in its biased or natural state. The prostatic stent-catheter system 1 in FIGS. 19–25 further includes at least one suture 42. In another embodiment, the suture 42 can be replaced with any tubular structure that is thin enough to pass through the external sphincter 54 without negatively impacting the operation of the external sphincter 54 such as a long membrane. The suture 42 or tubular structure can be useful when removing the prostatic stent 3 from the prostatic section of the urethra at some point after the prostate has resolved. To attach the suture 42 to the prostatic stent 3 one end of the suture 42 is threaded through the distal terminating end 4 of the prostatic stent 3. The suture 42 is intended to run parallel to the prostatic stent 3 and connecting segment 6 walls along the lumen to reduce the likelihood of catching and holding blood clots. The other end of the suture 42 can be attached or connected to a retaining device 44. The retaining device 44 serves as a recovery means if the prostatic stent 3 proximally migrates. The retaining device 44 is slidably adjustable along the entire length of the suture 42, thereby allowing the physician to be able to position the retaining device 44 either within or external to the meatus 60. In the disclosed embodiment, the retaining device 44 is located external to the meatus 60 to permit erections. The retaining device 44 in FIGS. 19–25 is a bead. Various other embodiments of retaining devices are possible. Some of the other possible embodiments of retaining devices are illustrated in FIGS. 26–28.

Figure 20:
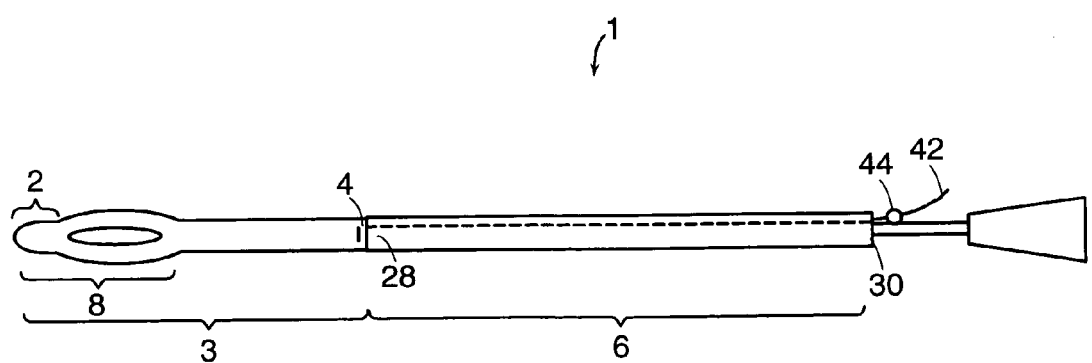
FIG. 20 is a schematic view of the prostatic stent-catheter system of FIG. 19 in an insertion configuration.
Figure 21:
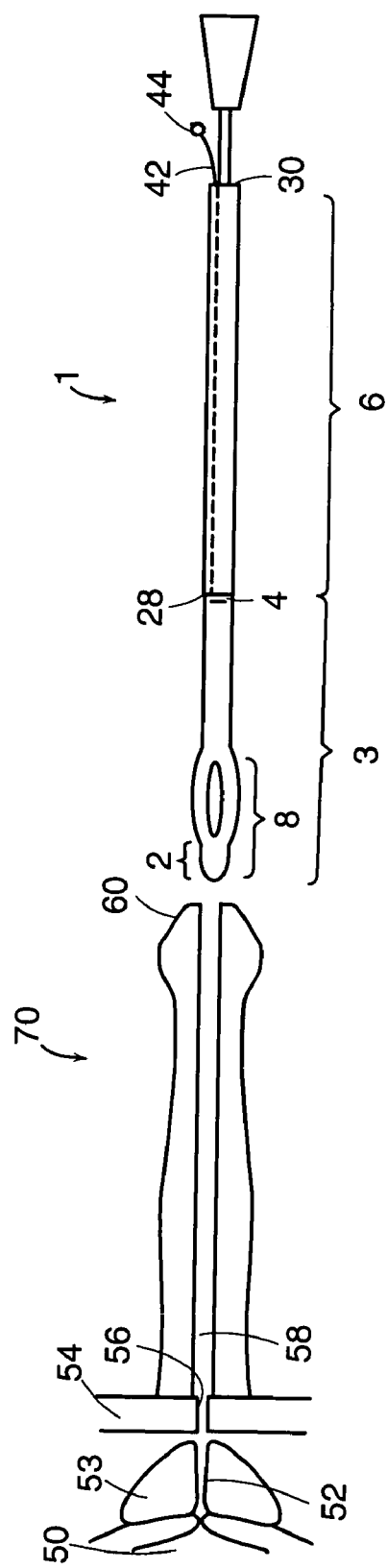
FIG. 21 is a schematic view of a male urinary system and the prostatic stent-catheter system of FIG. 20 prior to insertion.
Figure 22:
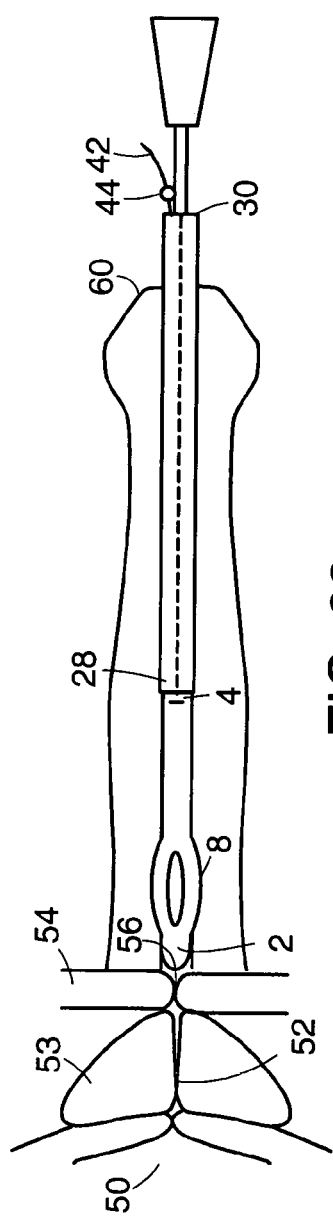
FIG. 22 is a schematic view illustrating insertion of the prostatic stent-catheter system of FIG. 20.
Figure 23:
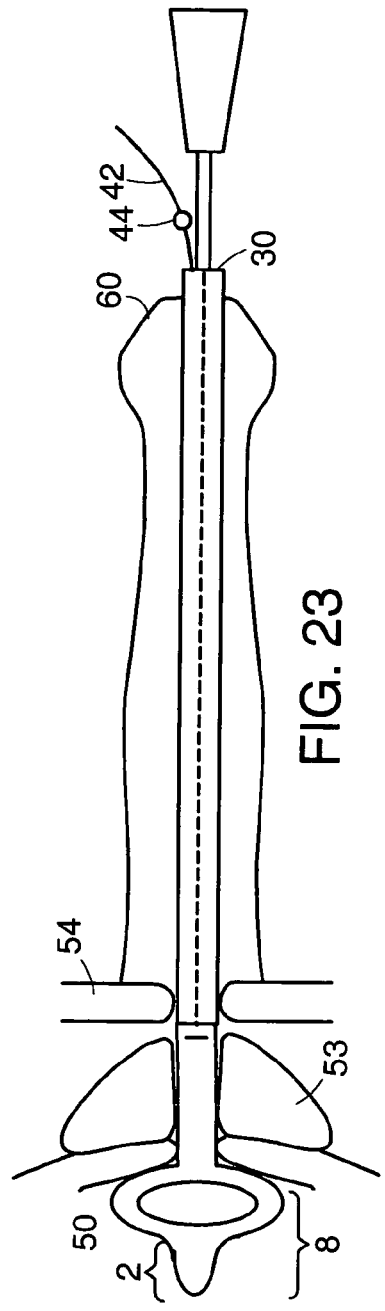
FIG. 23 is a schematic view illustrating proper placement of the prostatic stent-catheter system of FIG. 19.

Before a physician can insert the prostatic stent-catheter system 1 including a retaining member 8, the retaining member 8 must be collapsed. FIG. 20 shows a prostatic stent-catheter system 1 of a disclosed embodiment in an insertion or collapsed configuration. FIGS. 21–23 illustrate a method of inserting and placing a prostatic stent-catheter system 1. The remaining drawings, FIGS. 24–25 depict the decoupling of the prostatic stent 3 and the connecting segment 6 and the subsequent removal of the connecting segment 6 from a patient's urethra.

FIG. 21 shows an illustration of both the prostatic stent-catheter system 1 in the insertion configuration (i.e., collapsed retaining member), and a male urinary system 70. The male urinary system 70 including a urethra 58, an external sphincter 54, an opening to the external sphincter 56, a prostate 53, a prostatic section of the urethra 52, and a bladder 50. The point of insertion of the prostatic stent-catheter system 1 is the meatus 60.

To position the prostatic stent-catheter system 1 within a patient to relieve bladder outlet obstruction and to monitor a patient's bodily fluid excretions (post thermal prostate therapy, for example), a physician inserts the prostatic stent-catheter system 1 into a patient's urethra 58 through the meatus 60. This procedure is schematically illustrated in FIG. 22. The prostatic stent-catheter system 1 is advanced through the urethra until the prostatic stent 3 is substantially within the prostatic section of the urethra 52 with the retaining member 8 residing in the bladder 50. The physician can confirm proper placement of the prostatic stent-catheter system 1 by observing urine flowing through the connecting segment 6. FIG. 23 illustrates schematically the proper placement of a prostatic stent-catheter system 1.

The prostatic stent-catheter system 1 remains inside the male urinary system 70 until a decrease in prostate bleeding is observed and a physician decides that it is no longer necessary to monitor a patient's bodily fluid excretions. Even though a patient's bodily fluid excretions no longer require monitoring, the patient's prostate 53 may still be obstructed. To prevent bladder outlet obstruction and to promote prostate 53 recovery, a physician may decide to leave the prostatic stent 3 in position, and to remove only the connecting segment 6 portion of the prostatic stent-catheter system 1. To remove the connecting segment 6, the physician first decouples the prostatic stent 3 and connecting segment 6 by pulling on the connecting segment 6 (FIG. 24). The physician is then able to withdraw the connecting segment 6 from the urethra 58 (FIG. 25). Once the connecting segment 6 portion of the prostatic stent-catheter system 1 is removed, the patient's external sphincter opening 56 contracts, allowing the external sphincter 54 to operate normally and thus allowing the patient to control all bladder functions even though the prostatic stent 3 remains in place. The suture 42 attached to the prostatic stent 3 extends from the distal terminating end 4 through the urethra 58 and terminates just outside the meatus 60. The suture 42 is thin enough to pass through the contracted external sphincter opening 56 without negatively impacting the operation of the external sphincter or therefore the patient's bladder control. The removal of a prostatic stent 3 may be performed separately at some later time, by either pulling on the suture 42 or through endoscopic means.

Variations, modifications, and other implementations of what is described herein will occur to those of ordinary skill in the art without departing from the spirit and the scope of the invention. The invention is not to be limited by the preceding illustrative description.

What is claimed is:

1. A prostatic stent-catheter system for draining fluid from the bladder and through the prostate after prostate treatment, comprising:

(a) a stent comprising a body member including a distal terminating end, a proximal end portion, and a lumen extending within the body member, the body member sized for placement substantially within the prostatic section of the urethra with the distal terminating end located proximal of the external sphincter;

(b) a connecting segment comprising an elongated body member including a distal end located outside of a patient's body, a proximal end releasably joined to the distal terminating end, and a lumen which extends within the elongated body member and aligns with the lumen of the body member of the stent when the proximal end of the elongated body member of the connecting segment is releasably joined to the distal terminating end of the body member of the stent to form a single lumen through the pro static stent-catheter system; and (c) a member comprising a first portion and a second portion, the first portion fastened to the proximal end of the elongated body member and the second portion for slip fitting into the lumen of the body member at the distal terminating end to releasably join the proximal end of the elongated body member to the distal terminating end of the body member.

2. The prostatic stent-catheter system according to claim 1 wherein the stent further comprises a retaining member extending from the proximal end portion of the body member of the stent, wherein the retaining member is capable of holding the body member substantially within the prostatic section of the urethra, and the retaining member comprises a proximal end defining a ledge for receiving a pushing device.

3. The prostatic stent-catheter system according to claim 1 wherein the stent further comprises a retaining member extending from the proximal end portion of the body member of the stent, wherein the retaining member is collapsible and expandable, and the retaining member comprises a proximal end defining a ledge for receiving a pushing device.

4. The prostatic stent-catheter system according to claim 3 further comprising:

(a) the pushing device slidably receivable by the prostatic stent-catheter system, the pushing device including an insertion end and an external end, the pushing device sized to allow the insertion end to contact the retaining member of the stent while the external end remains outside the patient's body; and (b) a handle secured to the distal end of the elongated body member, the handle including at least one opening to allow fluid drainage out of the handle and including a mechanism attached to the pushing device to allow a physician to control the position of the pushing device within the lumen of the connecting segment and the lumen of the stent.

5. The prostatic stent-catheter system according to claim 4 wherein the mechanism has:

(a) a first position that extends the pushing device, resulting in the collapse of the retaining member of the stent;

(b) a second position that retracts the pushing device, resulting in the expansion of the retaining member of the stent; and (c) a third position that further retracts the pushing device, resulting in the absence of contact between the pushing device and the retaining member of the stent.

6. The prostatic stent-catheter system according to claim 4 wherein the insertion end of the pushing device is straight.

7. The prostatic stent-catheter system according to claim 1 wherein the stent comprises one or more protuberances to aid retention of the body member substantially within the prostatic section of the urethra.

8. The prostatic stent-catheter system according to claim 1 wherein the body member defines one or more side openings in communication with the lumen.

9. The prostatic stent-catheter system according to claim 4 wherein the pushing device further comprises a flange for engaging the ledge defined by the proximal end of the retaining member.

10. A method of placing a prostatic stent-catheter system, comprising the steps of:

(a) providing the prostatic stent-catheter system which comprises:

(i) a stent comprising a body member including a distal terminating end, a proximal end portion, and a lumen extending within the body member, the body member sized for placement substantially within the prostatic section of the urethra with the distal terminating end located proximal of the external sphincter;

(ii) a connecting segment comprising an elongated body member including a distal end located outside of a patient's body, a proximal end releasably joined to the distal terminating end, and a lumen which extends within the elongated body member and aligns with the lumen of the body member of the stent when the proximal end of the elongated body member of the connecting segment is releasably joined to the distal terminating end of the body member of the stent to form a single lumen through the prostatic stent-catheter system; and (iii) a member comprising a first portion and a second portion, the first portion fastened to the proximal end of the elongated body member and the second portion for slip fitting into the lumen of the body member at the distal terminating end to releasably join the proximal end of the elongated body member to the distal terminating end of the body member;

(b) inserting the prostatic stent-catheter system into the patient's urethra;

(c) positioning the stent substantially within the prostatic section of the urethra;

(d) monitoring fluid drainage through the stent and the connecting segment, and out of the distal end of the connecting segment located outside of the patient's body;

(e) decoupling the connecting segment from the stent; and (f) withdrawing the connecting segment completely from the urethra and patient's body.

11. A prostatic stent-catheter system for draining fluid from the bladder and through the prostate after prostate treatment, comprising:

(a) a stent comprising a body member including a distal terminating end, a proximal end portion, and a lumen extending within the body member, the body member sized for placement substantially within the prostatic section of the urethra with the distal terminating end located proximal of the external sphincter;

(b) a connecting segment comprising an elongated body member adapted to extend through the external sphincter to maintain the external sphincter open, the elongated body member including a distal end located outside of a patient's body, a proximal end releasably joined to the distal terminating end, and a lumen which extends within the elongated body member; and (c) a member comprising a first portion and a second portion, the first portion fastened to the proximal end of the elongated body member and the second portion for slip fitting into the lumen of the body member at the distal terminating end to releasably join the proximal end of the elongated body member to the distal terminating end of the body member.

12. The prostatic stent-catheter system according to claim 11 wherein the stent further comprises a retaining member extending from the proximal end portion of the body member of the stent, wherein the retaining member is collapsible and expandable.

* * * * *